United States Patent
Al-Ali

(10) Patent No.: US 9,480,422 B2
(45) Date of Patent: Nov. 1, 2016

(54) CYANOTIC INFANT SENSOR

(71) Applicant: MASIMO CORPORATION, Irvine, CA (US)

(72) Inventor: Ammar Al-Ali, San Juan Capistrano, CA (US)

(73) Assignee: MASIMO CORPORATION, Irvine, CA (US)

( * ) Notice: Subject to any disclaimer, the term of this patent is extended or adjusted under 35 U.S.C. 154(b) by 78 days.

(21) Appl. No.: 14/223,894

(22) Filed: Mar. 24, 2014

(65) Prior Publication Data
US 2014/0206963 A1    Jul. 24, 2014

Related U.S. Application Data

(63) Continuation of application No. 13/100,145, filed on May 3, 2011, now Pat. No. 8,682,407, which is a continuation of application No. 11/171,632, filed on Jun. 30, 2005, now Pat. No. 7,937,128.

(60) Provisional application No. 60/586,821, filed on Jul. 9, 2004.

(51) Int. Cl.
*A61B 5/1455* (2006.01)
*A61B 5/00* (2006.01)

(52) U.S. Cl.
CPC ......... *A61B 5/14551* (2013.01); *A61B 5/0059* (2013.01); *A61B 5/14552* (2013.01); *A61B 5/7271* (2013.01); *A61B 2503/04* (2013.01)

(58) Field of Classification Search
CPC ............ A61B 5/1455; A61B 5/14551; A61B 5/14552; A61B 5/72; A61B 5/7271
See application file for complete search history.

(56) References Cited

U.S. PATENT DOCUMENTS

| | | |
|---|---|---|
| 4,960,128 A | 10/1990 | Gordon et al. |
| 4,964,408 A | 10/1990 | Hink et al. |
| 5,041,187 A | 8/1991 | Hink et al. |
| 5,069,213 A | 12/1991 | Polczynski |
| 5,163,438 A | 11/1992 | Gordon et al. |
| 5,319,355 A | 6/1994 | Russek |
| 5,337,744 A | 8/1994 | Branigan |
| 5,341,805 A | 8/1994 | Stavridi et al. |

(Continued)

FOREIGN PATENT DOCUMENTS

| | | |
|---|---|---|
| WO | WO 97/03603 A | 2/1997 |
| WO | WO 02/35999 A | 5/2002 |
| WO | WO 02/089664 A | 11/2002 |

OTHER PUBLICATIONS

Reich, JD et al., "The use of pulse oximetery to detect congenital heart disease", Journal of Pediatrics, pp. 268-272, Mar. 2003.

*Primary Examiner* — Eric Winakur
(74) *Attorney, Agent, or Firm* — Knobbe, Martens, Olson & Bear LLP

(57) ABSTRACT

A pulse oximetry sensor comprises emitters configured to transmit light having a plurality of wavelengths into a fleshy medium. A detector is responsive to the emitted light after absorption by constituents of pulsatile blood flowing within the medium so as to generate intensity signals. A sensor head has a light absorbing surface adapted to be disposed proximate the medium. The emitters and the detector are disposed proximate the sensor head. A detector window is defined by the sensor head and configured so as to limit the field-of-view of the detector.

20 Claims, 7 Drawing Sheets

(56) References Cited

U.S. PATENT DOCUMENTS

| | | |
|---|---|---|
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| D361,840 S | 8/1995 | Savage et al. |
| 5,437,275 A | 8/1995 | Amundsen et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,584,296 A | 12/1996 | Cui et al. |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,830,136 A | 11/1998 | DeLonzor et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,018,673 A | 1/2000 | Chin et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,301,493 B1 | 10/2001 | Marro et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,423 B2 | 8/2002 | DeLonzor et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kianl et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,711,425 B1 | 3/2004 | Reuss |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,763,255 B2 | 7/2004 | DeLonzor et al. |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |

(56) References Cited

U.S. PATENT DOCUMENTS

| | | |
|---|---|---|
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 2004/0176670 A1* | 9/2004 | Takamura ......... A61B 5/14551 600/322 |

\* cited by examiner

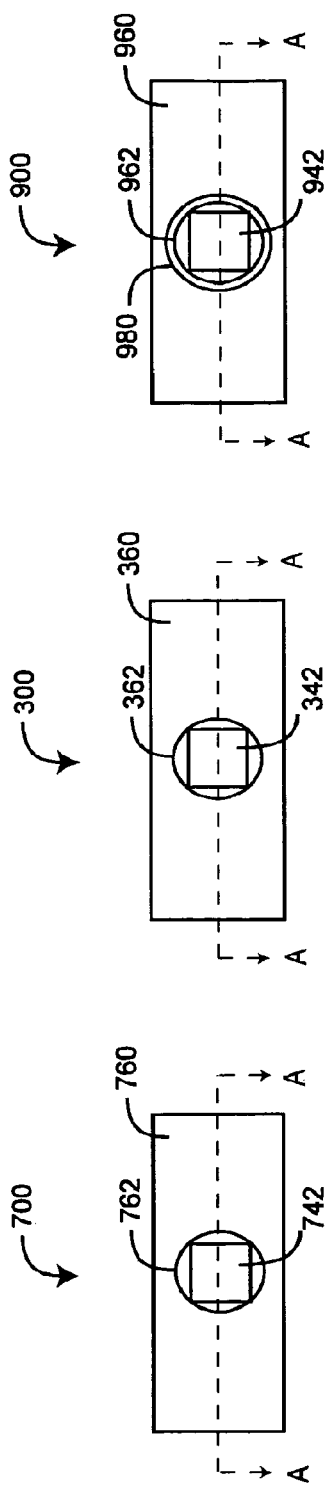
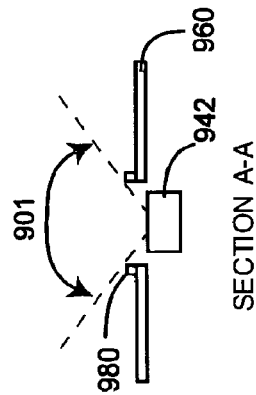
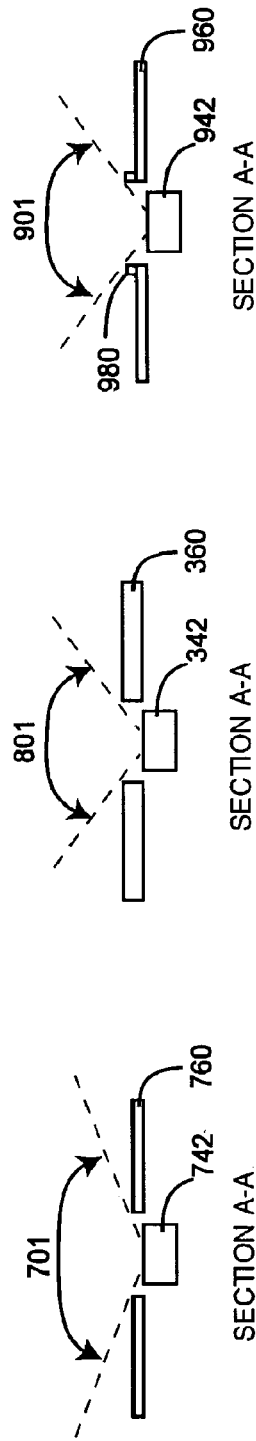
FIG. 9A
FIG. 9B
FIG. 8A
FIG. 8B
FIG. 7A (Prior Art)
FIG. 7B (Prior Art)

CYANOTIC INFANT SENSOR

CROSS-REFERENCE TO RELATED APPLICATION

The present application claims priority benefit under 35 U.S.C. §120 to, and is a continuation of U.S. patent application Ser. No. 13/100,145, filed May 3, 2011 entitled "Cyanotic Infant Sensor," now U.S. Pat. No. 8,682,407, which is a continuation of U.S. patent application Ser. No. 11/171,632, filed Jun. 30, 2005 entitled "Cyanotic Infant Sensor," now U.S. Pat. No. 7,937,128, which claims priority benefit under 35 U.S.C. §119(e) from U.S. Provisional Application No. 60/586,821, filed Jul. 9, 2004, entitled "Cyanotic Infant Sensor." The present application also incorporates the foregoing disclosures herein by reference.

BACKGROUND OF THE INVENTION

Cyanosis is a congenital condition in which blood pumped to the body contains less than normal amounts of oxygen, resulting in a blue discoloration of the skin. The most common cyanotic condition is tetralogy of Fallot, which is characterized by an abnormal opening, or ventricular septal defect, that allows blood to pass from the right ventricle to the left ventricle without going through the lungs; a narrowing, or stenosis, proximate the pulmonary valve, which partially blocks the flow of blood from the right side of the heart to the lungs; a right ventricle that is abnormally muscular; and an aorta that lies directly over the ventricular septal defect. Another cyanotic condition is tricuspid atresia, characterized by a lack of a tricuspid valve and resulting in a lack of blood flow from the right atrium to the right ventricle. Yet another cyanotic condition is transposition of the great arteries, i.e. the aorta originates from the right ventricle, and the pulmonary artery originates from the left ventricle. Hence, most of the blood returning to the heart from the body is pumped back out without first going to the lungs, and most of the blood returning from the lungs goes back to the lungs.

Pulse oximetry is a useful tool for diagnosing and evaluating cyanotic conditions. A pulse oximeter performs a spectral analysis of the pulsatile component of arterial blood so as to measure oxygen saturation, the relative concentration of oxygenated hemoglobin, along with pulse rate. FIG. 1 illustrates a pulse oximetry system 100 having a sensor 110 and a monitor 140. The sensor 110 has emitters 120 and a detector 130 and is attached to a patient at a selected fleshy tissue site, such as a thumb or toe. The emitters 120 project light through the blood vessels and capillaries of the tissue site. The detector 130 is positioned so as to detect the emitted light as it emerges from the tissue site. A pulse oximetry sensor is described in U.S. Pat. No. 6,088,607 entitled "Low Noise Optical Probe," which is assigned to Masimo Corporation, Irvine, Calif. and incorporated by reference herein.

Also shown in FIG. 1, the monitor 140 has drivers 150, a controller 160, a front-end 170, a signal processor 180, a display 190. The drivers 150 alternately activate the emitters 120 as determined by the controller 160. The front-end 170 conditions and digitizes the resulting current generated by the detector 130, which is proportional to the intensity of the detected light. The signal processor 180 inputs the conditioned detector signal and determines oxygen saturation, as described below, along with pulse rate. The display 190 provides a numerical readout of a patient's oxygen saturation and pulse rate. A pulse oximetry monitor is described in U.S. Pat. No. 5,482,036 entitled "Signal Processing Apparatus and Method," which is assigned to Masimo Corporation, Irvine, Calif. and incorporated by reference herein.

SUMMARY OF THE INVENTION

The Beer-Lambert law provides a simple model that describes a tissue site response to pulse oximetry measurements. The Beer-Lambert law states that the concentration $c_i$ of an absorbent in solution can be determined by the intensity of light transmitted through the solution, knowing the mean pathlength, $mpl_\lambda$, the intensity of the incident light, $I_{0,\lambda}$, and the extinction coefficient, $\epsilon_{i,\lambda}$, at a particular wavelength $\lambda$. In generalized form, the Beer-Lambert law is expressed as:

$$I_\lambda = I_{0,\lambda} e^{-mpl_\lambda \cdot \mu_{a,\lambda}} \qquad (1)$$

$$\mu_{a,\lambda} = \sum_{i=1}^{n} \epsilon_{i,\lambda} \cdot c_i \qquad (2)$$

where $\mu_{a,\lambda}$ is the bulk absorption coefficient and represents the probability of absorption per unit length. For conventional pulse oximetry, it is assumed that there are only two significant absorbers, oxygenated hemoglobin ($HbO_2$) and reduced hemoglobin (Hb). Thus, two discrete wavelengths are required to solve EQS. 1-2, e.g. red (RD) and infrared (IR).

FIG. 2 shows a graph 200 depicting the relationship between RD/IR 202 and oxygen saturation ($SpO_2$) 201, where RD/IR denotes the ratio of the DC normalized, AC detector responses to red and infrared wavelengths, as is well-known in the art and sometimes referred to as the "ratio-of-ratios." This relationship can be approximated from Beer-Lambert's Law, described above. However, it is most accurately determined by statistical regression of experimental measurements obtained from human volunteers and calibrated measurements of oxygen saturation. The result can be depicted as a curve 210, with measured values of RD/IR shown on an x-axis 202 and corresponding saturation values shown on a y-axis 201. In a pulse oximeter device, this empirical relationship can be stored in a read-only memory (ROM) for use as a look-up table so that $SpO_2$ can be directly read-out from an input RD/IR measurement. For example, an RD/IR value of 1.0 corresponding to a point 212 on the calibration curve 210 indicates a resulting $SpO_2$ value of approximately 85%.

Accurate and consistent pulse oximetry measurements on cyanotic infants have been difficult to obtain. An assumption inherent in the calibration curve 210 (FIG. 2) is that the mean pathlength ratio for RD and IR is constant across the patient population. That is:

$$mpl_{RD}/mpl_{IR} = C \qquad (3)$$

However, EQ. 3 may not be valid when cyanotic infants are included in that population. The reason may lie in what has been observed as abnormal tissue tone or lack of firmness associated with cyanotic defects, perhaps due to reduced tissue fiber. Such differences in tissue structure may alter the mean pathlength ratio as compared with normal infants. A cyanotic infant sensor addresses these problems by limiting variations in the RD over IR mean pathlength ratio and/or by providing a mean pathlength ratio measure so as to compensate for such variations. Alone or combined, these sensor apparatus and algorithms increase the accuracy and consistency of pulse oximetry measurements for cyanotic infants.

BRIEF DESCRIPTION OF THE DRAWINGS

FIGS. 7A-B are plan and cross-sectional sensor head views of a conventional pulse oximeter sensor;

FIGS. 8A-B and 9A-B are plan and cross-sectional sensor head views of cyanotic infant sensor embodiments.

DETAILED DESCRIPTION OF THE PREFERRED EMBODIMENTS

Figure 3A:
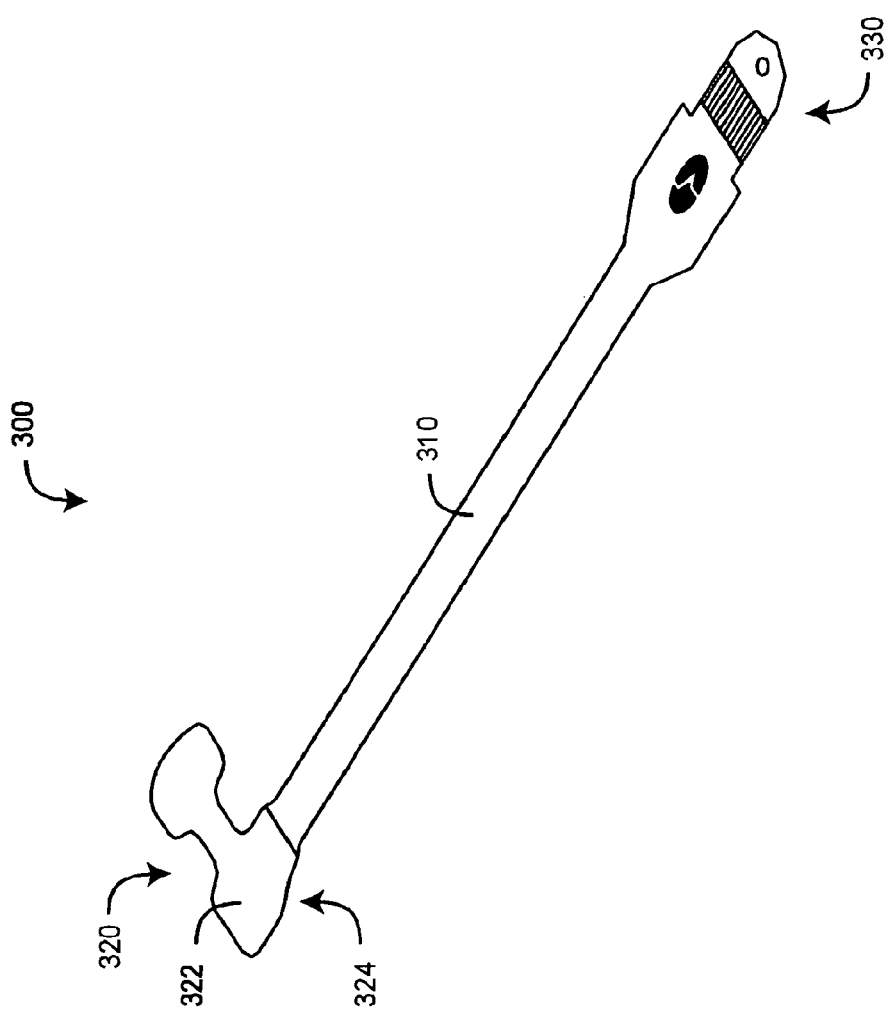
FIGS. 3A-B are a perspective and an exploded perspective views, respectively, of a cyanotic infant sensor embodiment.
Figure 3B:
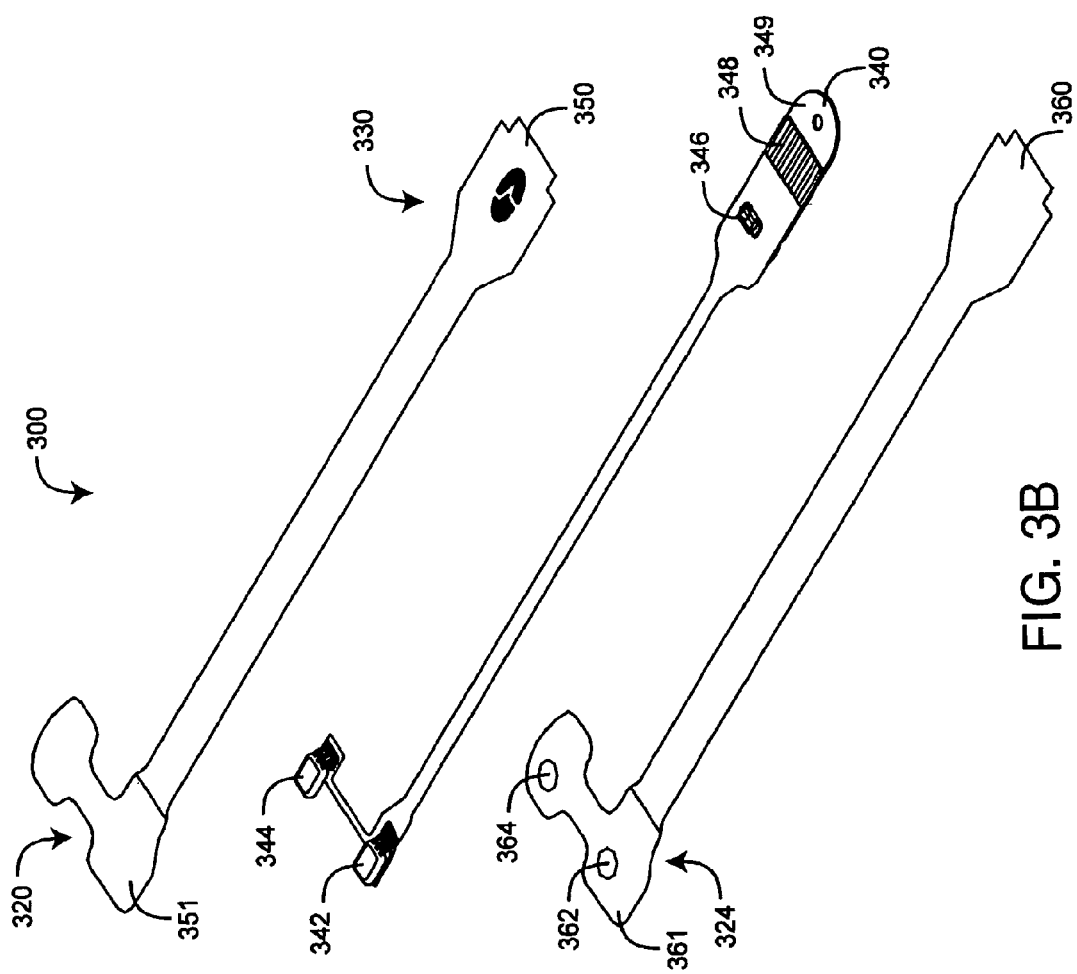

FIGS. 3A-B illustrate one embodiment of a cyanotic infant sensor. The sensor has a light absorbing surface, as described with respect to FIGS. 4-6, below. The sensor also has a detector window configured to limit the detector field-of-view (FOV), as described with respect to FIGS. 7-9, below. Advantageously, these features limit mean pathlength ratio variations that are particularly manifest in cyanotic patients.

The sensor emitters and detector are also matched so as to limit variations in the detector red over IR DC response, i.e. $RD_{DC}/IR_{DC}$, that are not attributed to variations in the mean pathlength ratio (EQ. 3). Such matching advantageously allows for measurement and calibration of the mean pathlength ratio, as described with respect to FIG. 10, below. In one embodiment, cyanotic infant sensors 300 are constructed so that:

$$\lambda_{RD} \approx c_1; \lambda_{IR} \approx c_2 \quad (4)$$

$$I_{0,RD}/I_{0,IR} \approx c_3; \text{ for } i_{DC}(RD), i_{DC}(IR) \quad (5)$$

$$RD_{DC}/IR_{DC} \approx c_4 \quad (6)$$

That is, sensors 300 are constructed from red LEDs and IR LEDs that are each matched as to wavelength (EQ. 4). The LEDs are further matched as to red over IR intensity for given DC drive currents (EQ. 5). In addition, the sensors 300 are constructed from detectors that are matched as to red over IR DC response (EQ. 6).

As shown in FIG. 3A, the sensor 300 has a body 310 physically connecting and providing electrical communication between a sensor head 320 and a connector 330. The sensor head 320 houses the emitters and detector and attaches to a patient tissue site. The connector mates with a patient cable so as to electrically communicate with a monitor. In one embodiment, a sensor head surface 324 is constructed of light absorbing material.

As shown in FIG. 3B, the sensor 300 has a face tape 330, a flex circuit 340 and a base tape 360, with the flex circuit 340 disposed between the face tape 330 and the base tape 360. The flex circuit 340 has a detector 342, an emitter 344 with at least two light emitting diodes (LEDs), an informa-tion element 346, and contacts 348 disposed on a connector tab 349. Neonatal sensors having a detector, LEDs, an information element, contacts and connector tab are described in U.S. Pat. No. 6,256,523 entitled "Low-Noise Optical Probes," which is assigned to Masimo Corporation, Irvine, Calif. and incorporated by reference herein. In one embodiment, the face tape 350 and base tape 360 are constructed of Betham tape having attached polyethylene head tapes 351, 361. In a particular embodiment, the base head tape 361 is made of black polyethylene, and the face head tape 351 is made of white polyethylene. In one embodiment, a clear tape layer is disposed on the base head tape 361 tissue side over the detector window 362. The base head tape 361 has a detector window 362 and an emitter window 364 each allowing light to pass through the base head tape 361. In one embodiment, the base head tape 361 has a 4 mil thickness and the flex circuit has a 10 mil thickness. The combined 14 mil material thickness functions to limit the detector FOV, as described with respect to FIGS. 6 and 8, below.

Figure 6:
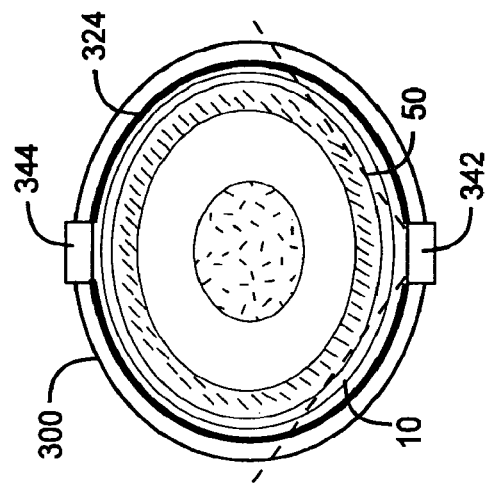
FIG. 6 depicts a cross-sectional view of a tissue site and an attached cyanotic infant sensor.
Figure 5:
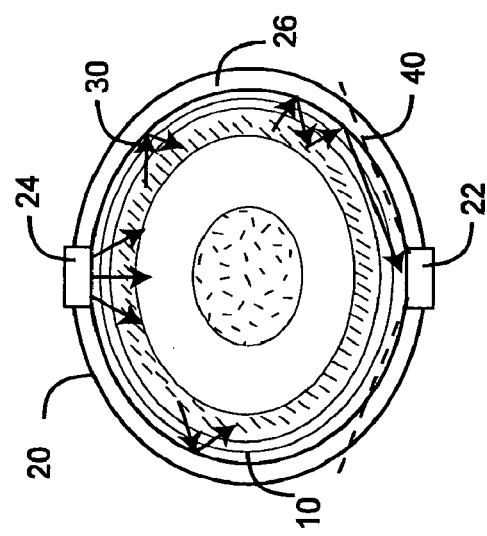
FIGS. 4-5 depict cross-sectional views of a tissue site and an attached pulse oximeter sensor, respectively.
Figure 4:
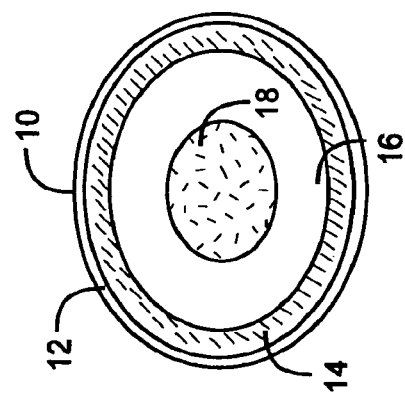

FIGS. 4-6 illustrate some of the pathlength control aspects of a cyanotic infant sensor 300. FIG. 4 depicts a fleshy tissue site 10 for sensor attachment, such as a finger or thumb 400. The tissue 10 has an epidermis 12, a dermis 14, subcutaneous and other soft tissue 16 and bone 18.

FIG. 5 depicts a conventional pulse oximetry sensor 20 having a detector 22, an emitter 24 and a tape 26 attached to the fleshy tissue 10. Transmitted light 30 propagating from the emitter 24 to the detector 22 that results in a significant contribution to pulse oximetry measurements passes through and is absorbed by the pulsatile blood in the dermis 14. A portion of the transmitted light 30 is scattered out of the epidermis 12 and reflected by the tape 26 back into the fleshy tissue 10. The detector field-of-view (FOV) 40 is relatively wide and, as a result, the detector responds to transmitted light 30 that has propagated, at least in part, outside of the fleshy tissue 10.

FIG. 6 depicts a cyanotic infant sensor 300 that is configured to limit variations in the mean pathlength ratio. In particular, the sensor 300 has a light absorbing tape inner surface 324 that reduces transmitted light reflection back into the tissue site 10, as described with respect to FIGS. 3A-B, above. Further, the detector 342 has a limited FOV 50 so as to reduce the detection of transmitted light that has propagated outside of the tissue site 10, as described in detail with respect to FIGS. 7-9, below.

FIGS. 8-9 illustrate cyanotic infant sensor embodiments having a limited detector field-of-view (FOV). FIGS. 7A-B illustrate a conventional sensor 700 having a tape portion 760, a detector window 762 and a detector 742 having a relatively wide FOV 701. In particular, the window thickness does little to restrict the FOV. FIGS. 8A-B illustrate one embodiment of a cyanotic infant sensor 300 having a material portion 360, a detector window 362 and a detector 342 having a restricted FOV 801. In particular, the material thickness 360 functions to define the FOV 801. In one embodiment, the material thickness 360 comprises a flex circuit thickness and a base head tape thickness, as described with respect to FIG. 3B, above. FIGS. 9A-B illustrate another embodiment of a cyanotic infant sensor 900 having a material portion 960, a detector window 962 and a detector 942 having a restricted FOV 901. In particular, an O-ring 980 deposed around the window 962 defines the FOV 901.

Figure 1:
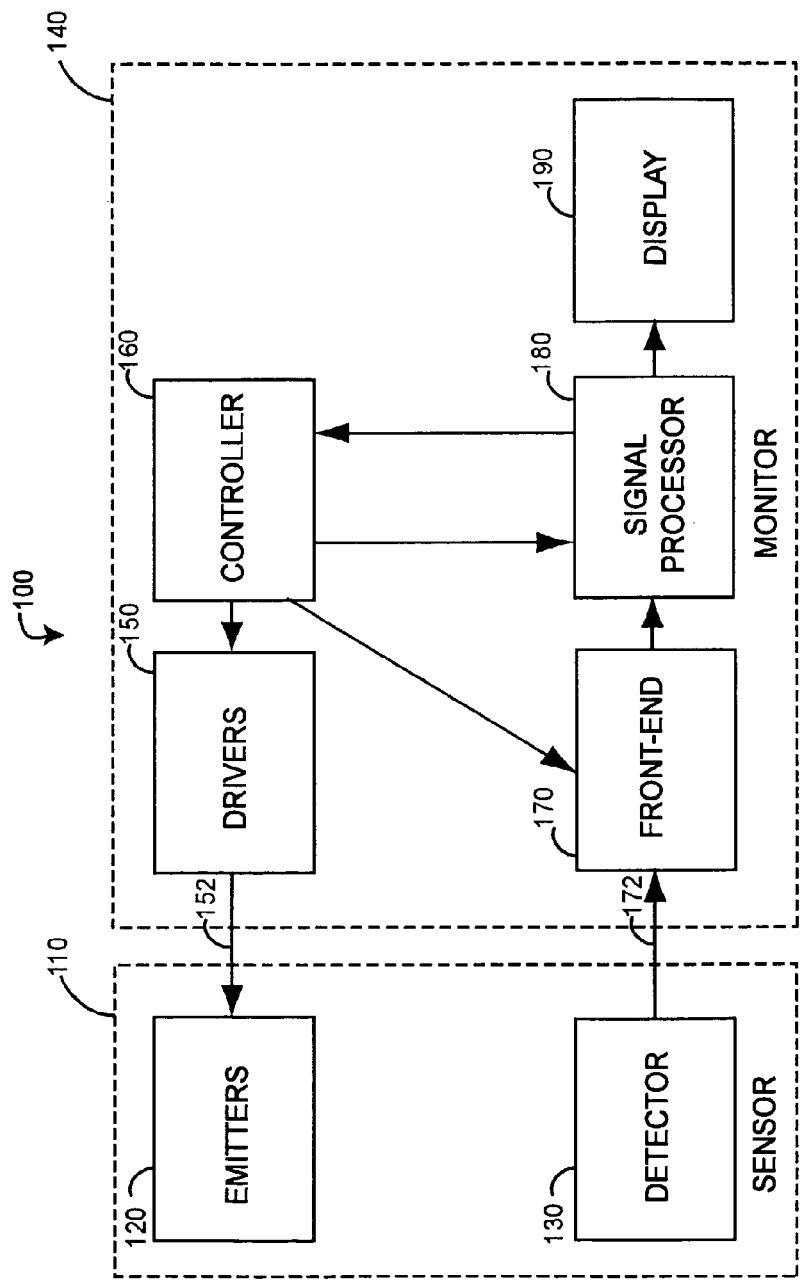
FIG. 1 is a block diagram of a prior art pulse oximetry system.
Figure 2:
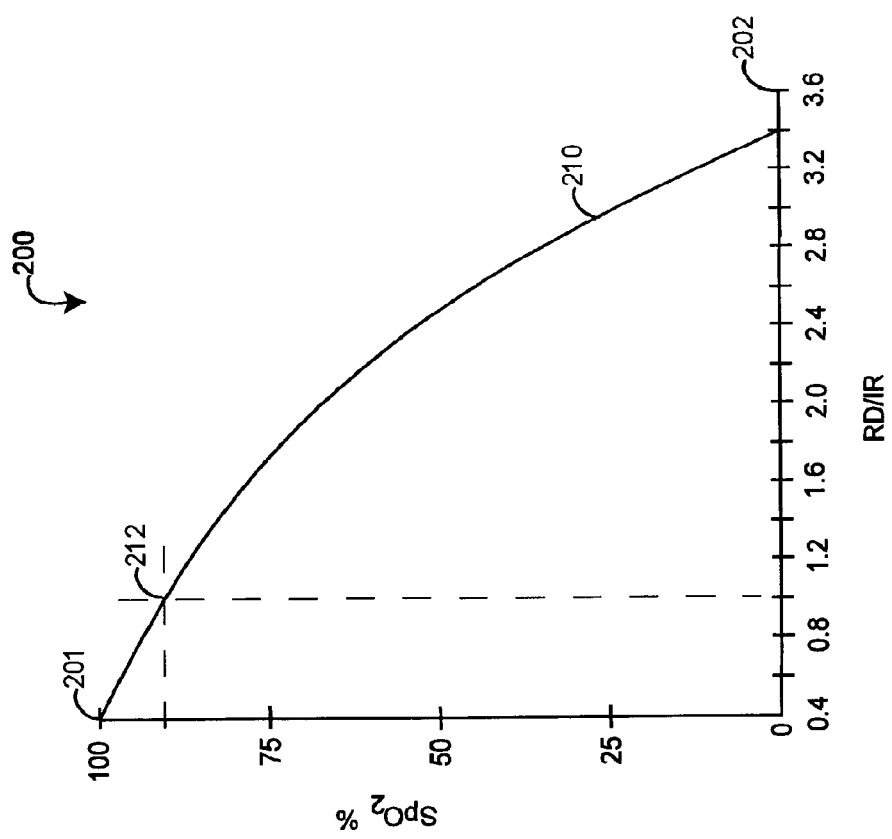
FIG. 2 is an exemplar graph of a conventional calibration curve.
Figure 10:
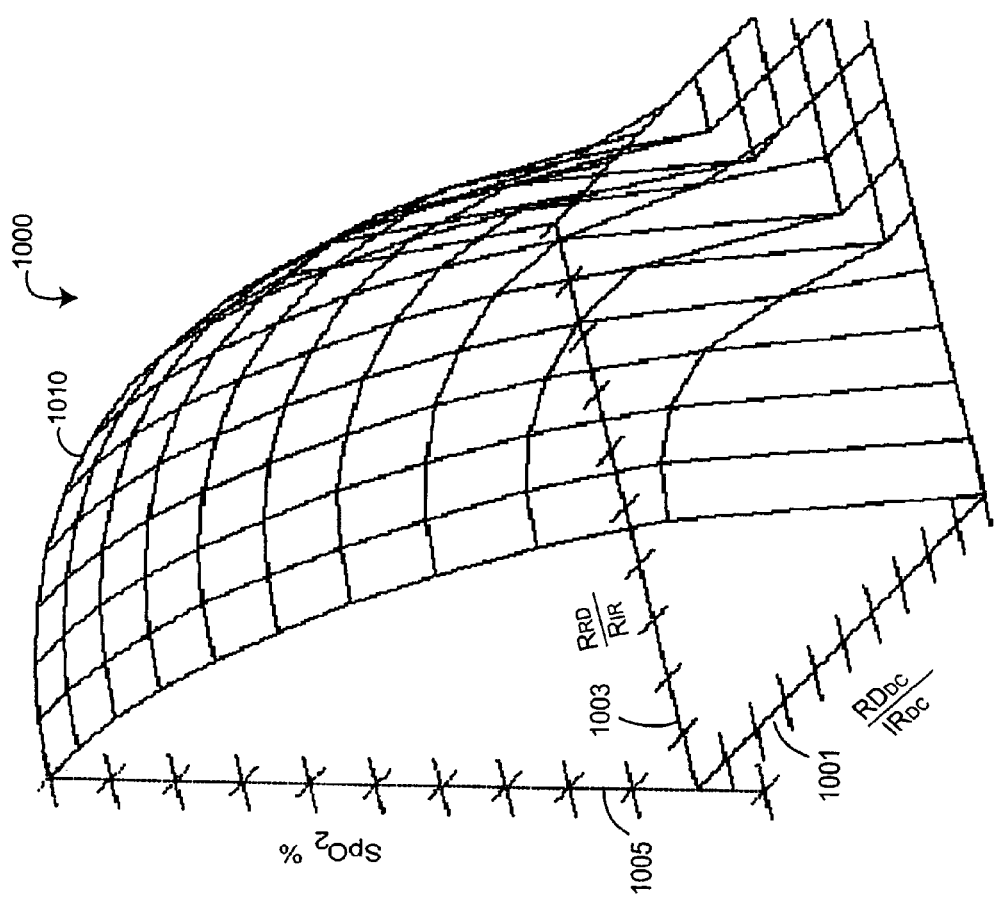
FIG. 10 is an exemplar graph of a calibration surface incorporating a mean pathlength ratio measure.

FIG. 10 depicts an exemplar calibration surface 1000 for a cyanotic infant sensor 300 (FIGS. 3A-B) calculated along a DC response ratio axis 1001, a ratio-of-ratios axis 1003 and a resulting oxygen saturation axis 1005. Matching the emitters and detectors, as described with respect to FIG. 3A, above, allows for pathlength calibration. In particular, variations in the detector DC response ratio ($RD_{dc}/IR_{dc}$) are attributed to variations in the mean pathlength ratio (EQ. 3). As such, a calibration surface is determined by statistical regression of experimental measurements obtained from human volunteers and calibrated measurements of oxygen saturation, as is done for a conventional calibration curve (FIG. 2). A calculated DC response ratio 1001 in combination with a conventionally calculated ratio-of-ratios 1003 is then used to derive an oxygen saturation 1005 for the calibration surface 1000.

A cyanotic infant sensor has been disclosed in detail in connection with various embodiments. These embodiments are disclosed by way of examples only and are not to limit the scope of the claims that follow. One of ordinary skill in art will appreciate many variations and modifications.

What is claimed is:

1. A method for determining a physiological parameter, the method comprising:
   receiving, from one or more detectors, one or more intensity signals responsive to light of a plurality of wavelengths attenuated by body tissue of a patient, said light emitted from a plurality of emitters, wherein said plurality of emitters and said one or more detectors are matched to reduce variations in a response of said one or more detectors that are not attributable to variations in a mean pathlength ratio of said light traveling through said body tissue between said plurality of emitters and said one or more detectors;
   electronically retrieving mapping data including a relationship between DC response ratio data, ratio-of-ratios data, and oxygen saturation data;
   electronically calculating a DC response ratio value responsive to said one or more intensity signals;
   electronically calculating a ratio-of-ratios value responsive to said one or more intensity signals; and
   electronically deriving an oxygen saturation measurement responsive to said mapping data.

2. The method of claim 1, comprising electronically displaying the patient's oxygen saturation responsive to said oxygen saturation measurement.

3. The method according to claim 1, wherein said calculating said DC response ratio comprises calculating said DC response ratio as a ratio of a detected incident intensity of the light at a first wavelength of said plurality of wavelengths to a detected incident intensity of the light at a second wavelength of said plurality of wavelengths.

4. The method according to claim 1, further comprising emitting said light from said plurality of emitters and receiving said light at one or more detectors.

5. The method according to claim 1, wherein a first subset of the plurality of emitters have been matched to transmit light at a first wavelength and a second subset of the plurality of emitters have been matched to transmit light at a second wavelength, wherein said matching of said emitters to said first and second wavelengths reduces variations in said response of said one more detectors not attributable to variations in said mean pathlength ratio of said light traveling through said body tissue between said plurality of emitters and said one or more detectors.

6. The method according to claim 1, wherein an emitted DC intensity ratio of said plurality of emitters for at least one predetermined DC drive current has been matched to a first predetermined constant, and wherein said matching of said emitted DC intensity ratio to said first predetermined constant further reduces variations in said response of said one more detectors not attributable to variations in said mean pathlength ratio of said light.

7. The method according to claim 6, further comprising receiving said light at one or more detectors and generating said intensity signals from said light received at said one or more detectors.

8. The method according to claim 7, wherein a DC response ratio of said one or more detectors having a first wavelength response over a second wavelength response for at least one predetermined DC incident intensity has been matched to a second predetermined constant, and wherein said matching of said DC response ratio to said second predetermined constant further reduces variations in said response of said one more detectors not attributable to variations in said mean pathlength ratio of said light.

9. The method according to claim 1, further comprising limiting a field-of-view of said one or more detectors so as to substantially limit said light received at said one or more detectors to portions of said light that propagate entirely through said body tissue.

10. A pulse oximeter comprising one or more processors configured to execute the method of claim 1.

11. The pulse oximeter of claim 10, further comprising the plurality of emitters configured to emit said light and the one or more detectors configured to detect said light.

12. The pulse oximeter of claim 10, further comprising a memory, said memory storing said mapping data.

13. The pulse oximeter of claim 12, wherein said memory comprises read only memory.

14. A pulse oximeter comprising:
   a sensor configured to output one or more intensity signals responsive to light attenuated by body tissue of a patient wearing said sensor, said sensor comprising plurality of emitters and one or more detectors, wherein said plurality of emitters and said one or more detectors are matched to reduce variations in a response of said one or more detectors that are not attributable to variations in a mean pathlength ratio of said light traveling through said body tissue between said plurality of emitters and said one or more detectors;
   a memory storing mapping data representing relationships between DC response data, ratio-of-ratios data, and oxygen saturation data; and
   a processor responsive to said output signals to determine a DC response and a ratio; said processor configured to determine a measurement value responsive to said relationships stored in said memory.

15. The pulse oximeter of claim 14, further comprising a patient monitor housing for housing said processor and said memory.

16. The pulse oximeter of claim 14, further comprising a sensor housing for housing said memory.

17. The pulse oximeter of claim 14, further comprising a display configured to display said measurement value.

18. The pulse oximeter of claim 14, wherein:
   a first subset of the plurality of emitters are matched to transmit light at a first wavelength and a second subset of the plurality of emitters are matched to transmit light at a second wavelength;
   an emitted DC intensity ratio of said plurality of emitters for at least one predetermined DC drive current is matched to a first predetermined constant; and
   a DC response ratio of said one or more detectors having a first wavelength response over a second wavelength response for at least one predetermined DC incident intensity is matched to a second predetermined constant;

wherein said matching of said emitters to said first and second wavelengths, said matching of said emitted DC intensity ratio to said first predetermined constant, and said matching of said DC response ratio to said second predetermined constant reduces variations in a response of said one more detectors not attributable to variations in a mean pathlength ratio of said light traveling through said body tissue between said plurality of emitters and said one or more detectors.

19. The pulse oximeter of claim 14, wherein said memory comprises read only memory.

20. A physiological sensor for outputting one or more intensity signals responsive to light attenuated by body tissue of a patient wearing, said sensor comprising:

a plurality of emitters having predetermined emitter operating characteristics, wherein a first subset of the plurality of emitters are matched to transmit light at a first wavelength and a second subset of the plurality of emitters are matched to transmit light at a second wavelength, and wherein an emitted DC intensity ratio of said plurality of emitters for at least one predetermined DC drive current is matched to a first predetermined constant; and one or more detectors having predetermined detector operating characteristics, wherein a DC response ratio of said one or more detectors having a first wavelength response over a second wavelength response for at least one predetermined DC incident intensity has been matched to a second predetermined constant;

wherein matching of said emitters to said first and second wavelengths, said matching of said emitted DC intensity ratio to said first predetermined constant, and said matching of said DC response ratio to said second predetermined constant collectively reduce variations in a response of said one or more detectors that are not attributable to variations in a mean pathlength ratio of said light traveling through said body tissue between said one or more emitters and said one or more detectors.

* * * * *